(12) United States Patent
Muravin et al.

(10) Patent No.: US 8,316,712 B2
(45) Date of Patent: Nov. 27, 2012

(54) QUANTITATIVE ACOUSTIC EMISSION NON-DESTRUCTIVE INSPECTION FOR REVEALING, TYPIFYING AND ASSESSING FRACTURE HAZARDS

(75) Inventors: Gregory Muravin, Netanya (IL); Boris Muravin, Netanya (IL); Ludmila Lezvinsky, Netanya (IL); Itzik Mizrahi, Netanya (IL)

(73) Assignee: Margan Physical Diagnostics Ltd. (IL)

( * ) Notice: Subject to any disclaimer, the term of this patent is extended or adjusted under 35 U.S.C. 154(b) by 253 days.

(21) Appl. No.: 12/950,830

(22) Filed: Nov. 19, 2010

(65) Prior Publication Data

US 2012/0125108 A1    May 24, 2012

(51) Int. Cl.
*G01H 1/00* (2006.01)
(52) U.S. Cl. ............... 73/587; 73/599; 73/602; 73/801
(58) Field of Classification Search .............. 73/587, 73/584, 592, 599, 602, 801
See application file for complete search history.

(56) References Cited

U.S. PATENT DOCUMENTS

| | | | |
|---|---|---|---|
| 3,713,127 A | 1/1973 | Keledy et al. |
| 3,858,439 A | 1/1975 | Nakamura |
| 3,946,600 A | 3/1976 | Rettig et al. |
| 4,033,179 A | 7/1977 | Romrell |
| 4,297,885 A | 11/1981 | Hein, Jr. et al. |
| 4,353,255 A | 10/1982 | Fukuda et al. |
| 4,428,236 A | 1/1984 | Votava et al. |
| 5,014,556 A | 5/1991 | Dunegan |
| 5,115,681 A | 5/1992 | Bouheraoua et al. |
| 5,270,950 A | 12/1993 | Cowley et al. |
| 5,526,689 A | 6/1996 | Coulter et al. |
| 5,714,687 A | 2/1998 | Dunegan |
| 5,929,315 A | 7/1999 | Dunegan |
| 6,041,656 A | 3/2000 | Dunegan |
| 6,062,083 A | 5/2000 | Dunegan |

(Continued)

FOREIGN PATENT DOCUMENTS

EP        2031386        3/2009

(Continued)

OTHER PUBLICATIONS

Muravin "Revealing, Identifying, and Assessing Flaws in Operating Equipment by the Acoustic Emission Image Recognition Method Under Strong Background Noise Condition" *Proceedings of Spie*, vol. 5472, Jan. 1, 2004 pp. 317-332.

(Continued)

*Primary Examiner* — J M Saint Surin
(74) *Attorney, Agent, or Firm* — Weaver Austin Villeneuve & Sampson LLP (57) ABSTRACT

Inspecting for fracture hazards by detecting a presence of at least one flaw development process in an equipment under inspection, the flaw development process being corrosion product nucleation and development, pitting, plastic deformation development, and/or micro-cracking. Detecting the presence of the flaw development process includes (a) determining at least one characteristic acoustic emission (AE) signature associated with a respective flaw development process, and (b) measuring an AE from each of a plurality of locations within the equipment. Presence of the respective flaw development process is identified only when the measured AE conforms to the characteristic AE signature within a predetermined tolerance. A fracture hazard is determined to exist only when (a) a quantity of the identified flaw development processes exceeds a first predetermined threshold and/or (b) a magnitude of at least one of the identified flaw development processes exceeds a second predetermined threshold.

22 Claims, 6 Drawing Sheets

U.S. PATENT DOCUMENTS

| | | | |
|---|---|---|---|
| 6,065,342 | A | 5/2000 | Kerr et al. |
| 6,173,613 | B1 | 1/2001 | Dunegan |
| 6,360,608 | B1 | 3/2002 | Dunegan |
| 6,386,038 | B1 | 5/2002 | Lewis, III et al. |
| 6,628,567 | B1 | 9/2003 | Prosser et al. |
| 6,823,736 | B1 | 11/2004 | Brock et al. |
| 6,962,082 | B2 | 11/2005 | Hashimoto et al. |
| 7,075,424 | B1 | 7/2006 | Sundaresan et al. |
| 7,103,507 | B2* | 9/2006 | Gorinevsky et al. ........... 702/184 |
| 7,182,519 | B2* | 2/2007 | Singh et al. .................... 384/448 |
| 7,379,845 | B2* | 5/2008 | Gorinevsky et al. .......... 702/184 |
| 7,435,004 | B2* | 10/2008 | Singh et al. .................... 384/448 |
| 7,458,267 | B2 | 12/2008 | McCoy |
| 7,698,943 | B2 | 4/2010 | Bohse et al. |
| 7,887,292 | B2 | 2/2011 | Kuhlmeier |
| 2001/0047691 | A1 | 12/2001 | Dzenis |
| 2003/0191605 | A1 | 10/2003 | Fujiyama et al. |
| 2003/0198425 | A1 | 10/2003 | Tapanes et al. |
| 2004/0025593 | A1 | 2/2004 | Hashimoto et al. |
| 2004/0030524 | A1 | 2/2004 | Jarrell et al. |
| 2010/0107765 | A1 | 5/2010 | Murakami et al. |
| 2011/0185814 | A1* | 8/2011 | Piccolo ........................... 73/587 |

FOREIGN PATENT DOCUMENTS

| | | |
|---|---|---|
| JP | 56-100359 | 8/1981 |
| JP | 61-284657 | 12/1986 |
| JP | 61-284658 | 12/1986 |
| JP | 03-191859 | 8/1991 |
| JP | 06-018491 | 1/1994 |
| JP | 07-063736 | 3/1995 |
| JP | 07-120440 | 5/1995 |
| JP | 07-134060 | 5/1995 |
| JP | 08-005614 | 1/1996 |
| JP | 09-300192 | 11/1997 |
| JP | 2000-258404 | 9/2000 |
| JP | 2010-181203 | 8/2010 |
| WO | WO 01/50122 | 7/2001 |

OTHER PUBLICATIONS

International Search Report dated Mar. 14, 2012 issued in PCT Application No. PCT/182011/002597.

Muravin, B., et al. (Oct. 2004) "Revealing Creep Associated and Industrial Flaws in Operating High Energy Piping by Quantitative Acoustic Emission Method", 13 pages.

Muravin, G. et al. (Nov. 1, 2004) "Revealing systems of Flaws in High-Pressure Reactors Operating Under Dynamic Pulse Loading", Proc. SPIE, vol. 5472, 409 (2004); Abstract, 1 page.

Muravin, B (2009) "Acoustic Emission Science and Technology", Journal of Building and Infrastructure Engineering of the Israeli Association of Engineers and Architects. 10 pages.

Muravin, G., et al. (May 26, 2004) "Revealing, Identifying, and Assessing Flaws in Operating Equipment by the Acoustic Emission Image Recognition Method Under Strong Background Noise Condition", Proc. SPIE, vol. 5472,317, 9 pages.

Muravin, B. (Nov. 2003) "The Application of Element Free Galerkin Method in the Investigation of Crack Interaction", thesis submitted for the degree of Doctor of Philosophy, Tel-Aviv University, 22 pages.

Muravin, B., et al. (2005) "Solution of a Dynamic Main Crack Interaction with a System of Micro-Cracks by the Element Free Galerkin Method", 21 pages.

Muravin, B, et al. (2006) "Spiral Weight for Modeling Cracks in Meshless Numerical Methods", 19 pages.

Muravin, B., et al. (2006) "Multiple Crack Weight for Solution of Multiple Interacting Cracks by Meshless Numerical Methods", 16 pages.

Muravin, B., "Quantitative Acoustic Emission Non Destructive Inspection Method as an On-Line Monitoring Tool for Preventive Maintenance of High Energy Piping in the Power Industry" [online] [retrieved on Feb. 19, 2010] Retrieved from: http://www.electricenergyonline.com/?page=show_article@mag-2&article-13, 6 pages.

Muravin, G., et al. (2008) "The Possibility of Revealing and Assessment Age Related Degradation and Industrial Flaws in High Chromium Steels Piping and Equipment by Quantitative Acoustic Emission Non-Destructive Method" Journal "Scientific Israel—Technological Advantages", vol. 10, No. 2, 17 pages.

Muravin, G. (2000) "Inspection, Diagnostics and Monitoring of Construction materials and Structures by Acoustic Emission Method" Minerva Press, ISBN 0754103749, 480 pages.

Muravin, B., "Acoustic Emission Method, History, Fundamentals, Application. A Short Presentation for Students", 45 pages.

Anastasopoulos, A., et al., "Using Acoustic Emission Technology for Detecting Structural Defects", 8 pages.

Ohtsu, et al. (Jul. 1, 2001) "Quantitative Damage Estimation of Concrete by Acoustic Emission", Construction and Building Materials, Abstract, 3 pages.

Morgan, Bryan C., et al. (Apr. 1999) "Inspection of Power Plant Headers Utilizing Acoustic Emission Monitoring", NDT&E International Journal, vol. 32, No. 3, 8 pages.

Niitsuma, H., et al. (1985) "Acoustic Emission Measurement of Geothermal Reservoir Cracks in Takinoue (Kakkonda) Field, Japan", Geothermic, vol. 14, Issue 4, pp. 5525-5538, Abstract, 2 pages.

Tonolini, F., et al. (1987)"General Review of Developments in Acoustic Emission Methods", Abstract, 1 page.

Coulter, J.E., et al. (Feb. 1988) "Acoustic Emission Monitoring of Fossil-Fuel Power Plants" Mater. Eval. vol. 46, No. 2, pp. 230-237, Abstract, 1 page.

Sinclair, A.C. E., et al. (May 1977) "Acoustic Emission Analysis During Fatigue Crack Growth in Steel", Materials Science and Engineering, vol. 28, Issue 2, pp. 263-273, Abstract, 2 pages.

Fan, Lei-Lei, et al. (2004) "Application of Acoustic Emission Technology in Condition Based Maintenance of Equipment", Abstract, 4 pages.

Pellionisz, P., et al. (1993) "Acoustic Emission Monitoring of Pressure Vessels" International Journal of Pressure Vessels and Piping, vol. 55, Issue 2, pp. 287-294, Abstract, 2 pages.

Matsunaga, I., et al. (Jul. 1989) "In Situ Stress Measurements by the Hydraulic Fracturing Method at Imaichi Pumped Storage power Plant, Tochigi, Japan", International Journal of Rock Mechanics and Mining Science & Geomechanics Abstracts, vol. 26, Issues 3-4, pp. 203-209, Abstract, 2 pages.

Jax, P., et al. (Apr. 1, 1989) "Acoustic Emission Inspections of Nuclear Components Considering Recent Research Programmes", Nuclear Engineering and Design, vol. 113, Issue 1, pp. 71-79, Abstract, 2 pages.

Runow, P., (1985) "The Use of Acoustic Emission Methods As Aids to the Structural Integrity Assessment of Nuclear Power Plants", International Journal of Pressure Vessels and Piping, vol. 21, Issue 3, pp. 157-207, Abstract, 2 pages.

Hirasawa, Taiji, et al. (Apr. 1999) "Nondestructive Evaluation of Aged Materials Used in Nuclear Power Plant by Magneto-Mechanical Acoustic Emission Technique" $7^{th}$ International conference on Nuclear Engineering, Tokyo, Japan, Apr. 19-23, 1999, 9 pages.

Tonolini, F., et al. (Jan. 1, 1985) "Acoustic Emission Examination of Power Plant Components", International Conference on Acoustic Emission, Lake Tahoe, NV, Abstract, 2 pages.

Prine, D.W. (Dec. 1976) "Inspection of Nuclear Power component Welds by In-Process Acoustic-Emission Monitoring" NDT International, vol. 9, issue 6, pp. 281-284, Abstract, 2 pages.

Lee, Jin Kyung, et al. (Sep. 2007) "Study on Damage Mechanism of Pipe Using Ultrasonic Wave and Acoustic Emission Technique", Key Engineering Materials, Volume: Progresses in Fracture and Strength of Materials and Structures, pp. 2415-2416, Abstract, 2 pages.

Rogers, L.M. (May 1980) "Plant Condition Monitoring", Minimizing the Cost of Maintenance, pp. 91-98, Abstract, 1 page.

Streicher, V.J. (Feb. 2003) "Acoustic Monitoring Systems—System Concept and Field Experience" Abstract, 3 pages.

Hyun, Jung-seob, et al. "DGZfP—Proceedings BB 90-CD Poster 8 EWGAE 2004 The Evaluation of Fatigue Crack Propagation by Acoustic Emission" [online] [retrieved on May 26, 2011] Retrieved from: http://citeseerx.ist.psu.edu/viewdoc/summary?doi=10.1.1.151.5869 2 pages.

Oh, K.H., et al. (Jan. 2006) "Detection and Evaluation of Localized Damage Under Creep-Fatigue Loading at 1000° F. Using Acoustic Emission Technique", Solid State phenomena, vol. 110, pp. 45-52, 8 pages.

Chang, Young Won, et al. (Oct. 2007) "Fatigue Life Evaluation of Pipe Welds in Power Plant Using Advanced Nondestructive Methods" Advanced Materials Research, vols. 26-28, pp. 1251-1254, Abstract, 2 pages.

Lee, Jin Kyung, et al. (Aug. 2007) "Propagation Characteristic of Elastic Wave Pipe,", Key Engineering Materials, vols. 345-346. Abstract, 2 pages.

Kumar, M. Mahesh (Nov. 2005) "Monitoring Crack Initiation in Metallic Components Through Acoustic Emission", Middle East Nondestructive Testing Conference, 5 pages.

Hirasawa, T., et al. (Oct. 1993) "Nondestructive Evaluation of Fatigue Damage on Low-Alloy Steel by Magnetic Technique", $12^{th}$ International conference on NBE in the Nuclear and Pressure Vessel Industries, Oct. 11-13, 1993, pp. 443-448, Abstract, 1 page.

Nam, Ki Woo, et al. (Aug. 2004) "Fracture Behaviors and Acoustic Emission Characteristics of Pipes with Local Wall Thinning", Abstract, 2 pages.

Holroyd, T.J., et al. (Feb. 2003) "Development of a Practical Acoustic Emission-Based Structural Monitoring System", Abstract, 2 pages.

Rodgers, John M., et al. (Mar. 1999) "Assess High-Energy Piping on Line—Before It's Too Late", 3 pages.

Jaske, Carl E., et al. (Nov. 2002) "Inspection and Remaining Life Evaluation of Process Plant Equipment", Process & Power Plant Reliability Conference, Nov. 13-14, 2002, 27 pages.

Rodriguez, Placid, et al. (Aug. 1997) "Development of In-service Inspection techniques for nuclear power plants in India", Abstract, 2 pages.

Lee, Jin Kylung (2008) "Corrosion Evaluation of Carbon Steels Using Nondestructive Technique", Abstract, 1 page.

Heida, J.H. (Mar. 2004) "Nondestructive Evaluation of Superalloy Specimens with a Thermal Barrier Coating", 14 pages.

Rao, A.K., et al. (1987) "Indian Developments in Ultrasonics and Acoustic Emission Methods", International Journal of Pressure Vessels and Piping, 28 (1-5), pp. 171-178, Abstract, 1 page.

Lackner, Gerald, et al. (2006) "Acoustic Emission: a Modern and Common NDT Method to Estimate Industrial Facilities", ECNDT 2006—We.3.6.4, 8 pages.

Jiang, Bing, et al. (Jul. 2005) "Mobile Monitoring for Distributed Infrastructures", Proceedings of the IEEE International Conference on Mechatronics & Automation, Jul. 2005, 6 pages.

Benz, A.E.G. (1998) "Use of Acoustic Emission Techniques for Detection of Discontinuities", Abstract, 2 pages.

Rodgers, John M. (2007) "Acoustic Emission Testing of Seam-Welded High Energy Piping Systems in Fossil Power Plants", 8 pages.

Raj, Baldev, et al. (2009) "Pressure Vessels and Piping: vol. IV: Inspection and Life Management" Abstract, 2 pages.

Verstrynge, Els, et al. (Mar. 2009) "Monitoring and Predicting Masonry's Creep Failure with the Acoustic Emission Technique", Abstract, 2 pages.

Ai, Qiong, et al. (2010) "Acoustic Emission of Fatigue Crack in Pressure Pipe Under cyclic Pressure", Abstract, 2 pages.

Rodgers, John, et al. (Jul. 2002) "Acoustic Emission Monitoring of Fossil High Energy Piping", Sixth EPRI Piping and Bolting Inspection Conference, 29 pages.

\* cited by examiner

Example of an experimentally determined characteristic acoustic emission signature: Energy vs. Average frequency three-dementia probability density graphs (a), their view from the top (b) and ellipses of dispersion (c) of the AE signals flow associated with background noise (1), corrosion product nucleation (2), pitting (3), plastic deformation development (4), and corrosion-fatigue micro-cracking

FIG. 3

Example of an experimentally determined, normalized, plot of ellipses of dispersion of AE signals flow "Energy-Hit rate" corrosion development. It can be seen that speed of corrosion development in test samples 4,5,6 are higher than in test samples 1,2, and 3.

AE signals Energy (a), Average frequency (b) and Amplitude (c) at different distance from the corroded zones as a result of attenuation.

FIG. 6

QUANTITATIVE ACOUSTIC EMISSION NON-DESTRUCTIVE INSPECTION FOR REVEALING, TYPIFYING AND ASSESSING FRACTURE HAZARDS

FIELD OF THE INVENTION

The field of the invention relates in general to non-destructive inspection for revealing, typifying, and assessing fracture hazards, and, in particular, to use of quantitative acoustic emission non-destructive inspection (QAE NDI) techniques for revealing, typifying, and assessing one or more flaw development processes associated with corrosion product nucleation and development, pitting, plastic deformation development, micro-cracking in equipment such as high energy piping complexes and components.

BACKGROUND

Fracture hazards in equipment such as high energy piping complexes and components may arise from flaw development processes such as electro-chemical corrosion, corrosion product nucleation and development, pitting, plastic deformation development, and micro-cracking resulting, for example, from corrosion-fatigue. These flaw development processes may accelerate fracture development, particularly in the case of a material subject to joint action of corrosion and cyclic loading. As a result, a failure may occur at substantially lower loads and/or after a shorter time than would be predicted in the absence of the flaw development processes.

Fracture hazard risk is influenced by equipment design and operating regime. For example, corrosion-fatigue of steel piping may be influenced by interaction with water or steam chemistry and/or oxygen, and the presence of stress concentrators. In addition, multiple temperature cycles in certain environments may result in oxide cracking, crack formation and development in the steel under the cracked scale layer, and, consequently, acceleration of material property degradation. As a further example, high speed steam flow carrying scale particles may cause erosion and accelerate oxide film delaminating and spoliation.

Non-destructive inspection (NDI) methods of conventional types are inadequate to determine whether operating structures have suffered hazardous damage due to such flaw development processes. In particular, for example, known methods are impractical for overall inspection of micro- and macro-flaws in complex and large-scale high energy piping complexes and similar equipment. As a result, catastrophic failures of, for example, chemical and fossil fuel power plants' main steam piping, and hot and cold reheat piping, chemical reactors' piping, and technological piping of chemical plants are not uncommon. Such failures present a serious economic and human safety hazard. In many instances, non-destructive and destructive evaluation of failed components demonstrated conclusively that the cause of failure was related to electro-chemical corrosion, pitting, plastic deformation development, and corrosion-fatigue micro-cracking. Conventional NDI techniques, unfortunately, are incapable of revealing, locating, identifying and assessing individual and interacting flaws with low and high stress intensity according to fracture mechanics criteria in equipment such as operating high energy piping complexes and components. As a result, structural elements that exhibit no signs of significant damage detectable by conventional methods may nevertheless represent future—even imminent—hazards. Thus, there is a significant unmet need for techniques to identify such propagating flaw development processes in time to mitigate the hazard and prevent catastrophic failure.

The present inventors have developed improved techniques for revealing flaws in reinforced concrete structures and for the diagnosis of creep in high energy piping during operation. QAE NDI is based on the fact that structures and materials undergoing deformation and flaw-development processes emit acoustic emissions (AE), in particular, sound and ultrasound waves. These AE, after acquisition by piezoelectric sensors, for example, may be digitized and analyzed. The analysis can reveal the location of flaws, their type and danger level. Since flaw development occurs under load, the consequent acoustic emission signals may be acquired during operation, pressure test, or cool down of the high energy piping. Muravin, G., "Inspection, Diagnostics and Monitoring of Construction Materials and Structures by the Acoustic Emission Method", 2000, Minerva Press, London, 480 pages, the disclosure of which is hereby incorporated in its entirety into the present application.

A number of known acoustic emission NDI techniques are disclosed by Coulter, et al., U.S. Pat. No. 5,526,689 (hereinafter, "Coulter") and Brock, et al., U.S. Pat. No. 6,823,736 (hereinafter, "Brock"). As identified by Brock, for example, "active" acoustic emission NDI systems employ an external excitation source (e.g., an ultrasonic probe signal) to impinge a sample under study. In such an active system, an acoustic transducer receives an acoustic emission signal from the test sample that resulted from perturbation of the original probe signal due to interfaces, structural changes or defects in the material. Disadvantages of NDI systems that use such active systems include complexity in quantitative analysis due to the need to decouple parasitic acoustic signals between the source and the detectors, and risk that the external excitation source signal may cause or accelerate damage to the sample under study. Brock further discloses known "passive" systems which use an acoustic detector but no acoustic or other external excitation source. According to Brock, such known passive systems suffer several disadvantages: (i) they may only be used to estimate the amount of damage in the material or how long a component will last; (ii) signals are typically smaller because there is no means to increase the level of the stimuli to increase signals; and (iii) because service environments are very noisy, and acoustic emission signals tend to be very weak, signal discrimination and noise reduction are difficult. Brock, 1:7-34.

For the foregoing reasons, and because the energy of acoustic emission signals associated with flaw development processes such as corrosion product nucleation and development, pitting, plastic deformation development, and micro-cracking is very low, passive acoustic emission NDI techniques have not been previously used for detection of such processes, notwithstanding the potential advantages of such methods with respect to active acoustic emission NDI techniques.

SUMMARY OF THE INVENTION

The present inventors have recognized that certain fracture hazards may be prevented by identifying, using QAE NDI techniques, the presence of corrosion product nucleation and development, pitting, plastic deformation development, and micro-cracking and/or by evaluating the rates at which such processes are developing. Advantageously, the QAE NDI methods disclosed hereinbelow may be of a passive type, thereby negating necessity of an external excitation source. The present methods permit revealing, recognizing and assessing multiple indications of corrosion-fatigue development and crack-like flaws, thereby enabling an improved assessment of the condition and forecast of the remaining life of operating equipment such as, for example, high energy piping.

In an embodiment, revealing, recognizing and assessing fracture hazards of corrosion product nucleation and development, pitting, plastic deformation development, and micro-cracking are performed by (i) detecting a presence of a flaw development process in an inspected equipment, where the flaw development process consists of corrosion product nucleation and development, pitting, plastic deformation development, and/or micro-cracking. Detecting a presence of a flaw development process may consist of (a) recording acoustic emission (AE) data of continuous AE and burst AE measured in a number of zones, the zones being known, as a result of visual inspection, local non-destructive inspection and/or metallurgical investigation, to be experiencing the flaw development process. The number of zones may be at least six, and the acquired AE data may consist of AE signal characteristics of amplitude, energy, and frequency measured at each zone; (b) determining AE signal transmission attenuation by recording AE data comprising AE signal characteristics of amplitude, energy, and frequency at different distances from each zone, the AE signal transmission attenuation characterizing kinetics of flaw development as a function of distance from the zone; (c) separating a plurality of AE signals associated with each flaw development process from background noise, using Gaussian shaped distribution; (d) determining, for at least one selected flaw development process, a characteristic AE signature by constructing a probability density graph and a plurality of ellipses of dispersion, where each ellipse of dispersion bounds a sheaf of AE signal properties associated with the characteristic AE signature; and the sheaf of AE signal properties is selected from the group consisting of energy vs. average frequency, amplitude vs. average frequency, and energy vs. hit rate; (e) creating a database of characteristic AE signatures by combining the information from each process described in (c), for a plurality of specific operational conditions; (f) measuring AE signals from each of a plurality of locations within the equipment; and (ii) comparing, for each location, said measured AE signals, corrected for said attenuation, with the characteristic AE signatures in the database; (iii) identifying a presence of the flaw development process only when the measured AE conforms to a characteristic AE signature in the database within a predetermined tolerance; and (iv) determining an intensity of the flaw development process by comparing a measured AE energy vs. hit rate with ellipses of dispersion of energy vs. hit rate from the database.

In another embodiment, the inspected equipment is a main steam (MS) piping, hot reheat (HRH) piping or cold reheat (CRH) piping of a fossil power plant, technological piping of a chemical plant, and/or other operating and large-scale high energy piping complex or components.

In a further embodiment, the detecting step is a passive operation performed while avoiding use of an external excitation load source.

In a yet further embodiment, the characteristic AE signature is an experimentally determined ellipse of dispersion.

In an embodiment, inspecting for fracture hazards in an equipment under inspection is performed by (i) detecting a presence of at least one flaw development process in the equipment wherein the flaw development process comprises at least one of corrosion product nucleation and development, pitting, plastic deformation development, and micro-cracking. Detecting a presence of at least one flaw development process may consist of (a) determining at least one characteristic acoustic emission (AE) signature associated with a respective flaw development process; (b) measuring AE signals from each of a plurality of locations within the equipment, the AE signals consisting of continuous AE signals associated with at least one flaw development process, burst AE signals associated with at least one flaw development process, and background noise; and, for each location, (1) separating at least one of the burst AE and the continuous AE signals associated with flaw development from background noise; (2) comparing the at least one of the burst AE and the continuous AE signals associated with flaw development with the characteristic AE signature; and (3) identifying the presence of one or more respective flaw development processes associated with one or more of the plurality of locations only when the at least one of the burst AE and the continuous AE signals associated with flaw development conforms to the characteristic AE signature within a predetermined tolerance; and (ii) determining that a fracture hazard exists, only when (a) a quantity of the identified flaw development processes exceeds a first predetermined threshold and/or (b) a magnitude of at least one of the identified flaw development processes exceeds a second predetermined threshold.

In another embodiment, the inspected equipment consists of a main steam (MS) piping, hot reheat (HRH) piping or cold reheat (CRH) piping of a fossil power plant, technological piping of a chemical plant, and/or other operating and large-scale high energy piping complex or components.

In a further embodiment, the detecting step is a passive operation performed while avoiding use of an external excitation load source.

In a still further embodiment, the at least one characteristic AE signature is an experimentally determined ellipse of dispersion. The experimentally determined ellipse of dispersion for each flaw development process may be determined by analysis of data acquired of at least one of continuous and burst AE in a number of zones known to be experiencing the failure process.

In an embodiment, the experimentally determined ellipse of dispersion bounds a sheaf of AE signal properties associated with the characteristic AE signature. The sheaf of AE bounded signal properties may consist of (i) energy vs. average frequency and/or (ii) amplitude vs. average frequency. The experimentally determined ellipse of dispersion may be determined by measurements in at least six zones known to be undergoing flaw development processes.

In a further embodiment, the at least one characteristic AE signature consists of an ellipse of dispersion relating AE signal energy vs. hit rate, and further comprising determining an intensity of the flaw development process by comparing a measured AE signal energy vs hit rate with said ellipse describing AE signal energy vs. hit rate.

Still further details of these and other embodiments of the invention are described hereinbelow.

BRIEF DESCRIPTION OF THE DRAWINGS

The present invention is illustrated by way of example, and not limitation, in the figures of the accompanying drawings, in which.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

DETAILED DESCRIPTION

Disclosed hereinbelow are techniques for mitigating fracture hazards using quantitative acoustic emission non-destructive inspection (QAE NDI) techniques. The techniques may be advantageously employed to periodically inspect the condition of high energy piping systems and other industrial complexes and/or components (hereinafter, "equipment"), without interrupting their normal operation.

Figure 1:
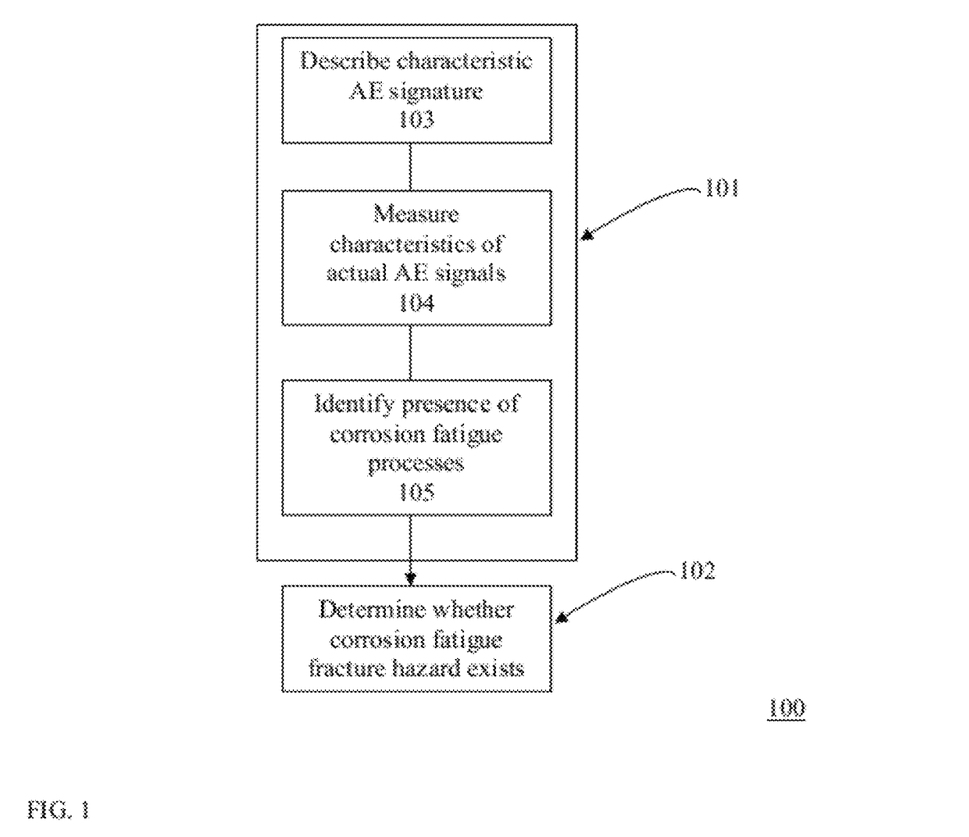
FIG. 1 presents a flow chart illustration of a method embodiment.

Referring now to FIG. 1, a method embodiment 100 for inspecting for fracture hazards in an equipment under test will be described. The method may be considered as having two main steps, a detection step 101 and a determination step 102.

In an embodiment, detection step 101 may consist of detecting a presence of at least one flaw development process in the equipment under inspection. The flaw development process may consist of corrosion product nucleation and development, pitting, plastic deformation development, and micro-cracking. The equipment may be, for example, main steam (MS) piping, hot reheat (HRH) piping or cold reheat (CRH) piping of a fossil power plant; technological piping of a chemical plant; or other operating and large-scale high energy piping complex, or components thereof.

In performing detection step 101, a characteristic acoustic emission (AE) signature associated with a respective flaw development process may first be described, step 103. The inventors have found that each respective flaw development process (e.g., corrosion product nucleation and development, pitting, plastic deformation development, and micro-cracking) may be associated with a characteristic AE signature, as described in further detail hereinbelow.

Second, characteristics of actual AE signals from the equipment may be measured, step 104. In an embodiment, AE signals may be measured from a number of locations, using sensors installed, for example, on external surfaces of the equipment. In an embodiment, the sensors may be piezoelectric sensors. Advantageously, measured characteristics of AE signals may include energy (E), amplitude (A), frequency (f), average frequency ($F_{ave}$), count rate (H) and/or other characteristics. The locations for sensor installation may be selected so that zones of reliable listening are overlapped and include most suspected zones of corrosion and pitting development (potentially corroded zones, weld joints, leaking lines, etc.). Advantageously, no fewer than six locations may be selected. The sensitivity of installed AE system, including, for example, sensors, preamplifiers, connections, etc. may be checked by a noise generator capable of creating signals similar to continuous and burst AE.

As used herein, and in the claims, the term "continuous AE" refers to such AE signals wherein the frequency of elementary defect process events, which lead to the appearance of stress waves, is high, while the energy realized by any single event is small. The inventors have found that, in operated high energy piping, for example, elementary defect process events resulting from temperature, pressure, steam flow variation, pipes vibration, etc. create such continuous AE as well as the burst AE. The appearance of continuous AE may be related to various processes of plastic deformation development. As used herein, and in the claims, the term "burst AE" refers to such AE signals wherein the signals have a discrete character, and the energy of each signal is generally one or more orders of magnitude higher than a continuous AE signal.

AE measurements of installed equipment, including, for example, chemical and fossil fuel power plants' main steam piping, and hot and cold reheat piping, chemical reactors' piping, and technological piping of chemical plants may be carried out during operation, shut down, as well as during hydraulic tests of the equipment. Advantageously, AE measurements may have increased sensitivity as a result of passively recording both continuous and burst AE, while avoiding use of an external excitation source.

Third, the presence of the respective flaw development process may be identified, step 105. In an embodiment, one or more measured AE signals may be compared with the characteristic AE signature as determined in step 103. When the measured AE signal(s) conform(s) to the characteristic AE signature within a predetermined tolerance a presence of a respective flaw development process may be identified.

In performing determination step 102, a fracture hazard may be determined to exist when at least one of (i) a quantity of the identified flaw development processes and/or (ii) a magnitude of at least one of the flaw development processes exceeds a respective predetermined threshold. Advantageously, each respective predetermined threshold permits distinguishing, at least, between hazardous and non-hazardous flaw development processes. The predetermined threshold may be determined, using criteria developed from conventional techniques of, for example, metallurgy and structural analysis, in addition to the techniques described herein.

In an embodiment, determination step 102 may include determining that a fracture hazard exists when a rate of development of at least one of the identified flaw development processes exceeds a rate threshold.

As noted hereinabove, the inventors have discovered that a characteristic AE signature may be associated with each of such flaw development processes as, at least, corrosion product nucleation and development, pitting, plastic deformation development, and micro-cracking. The associated AE signatures may be mutually distinguishable, as well as distinguishable from background noise and the AE of other processes.

Figure 2:
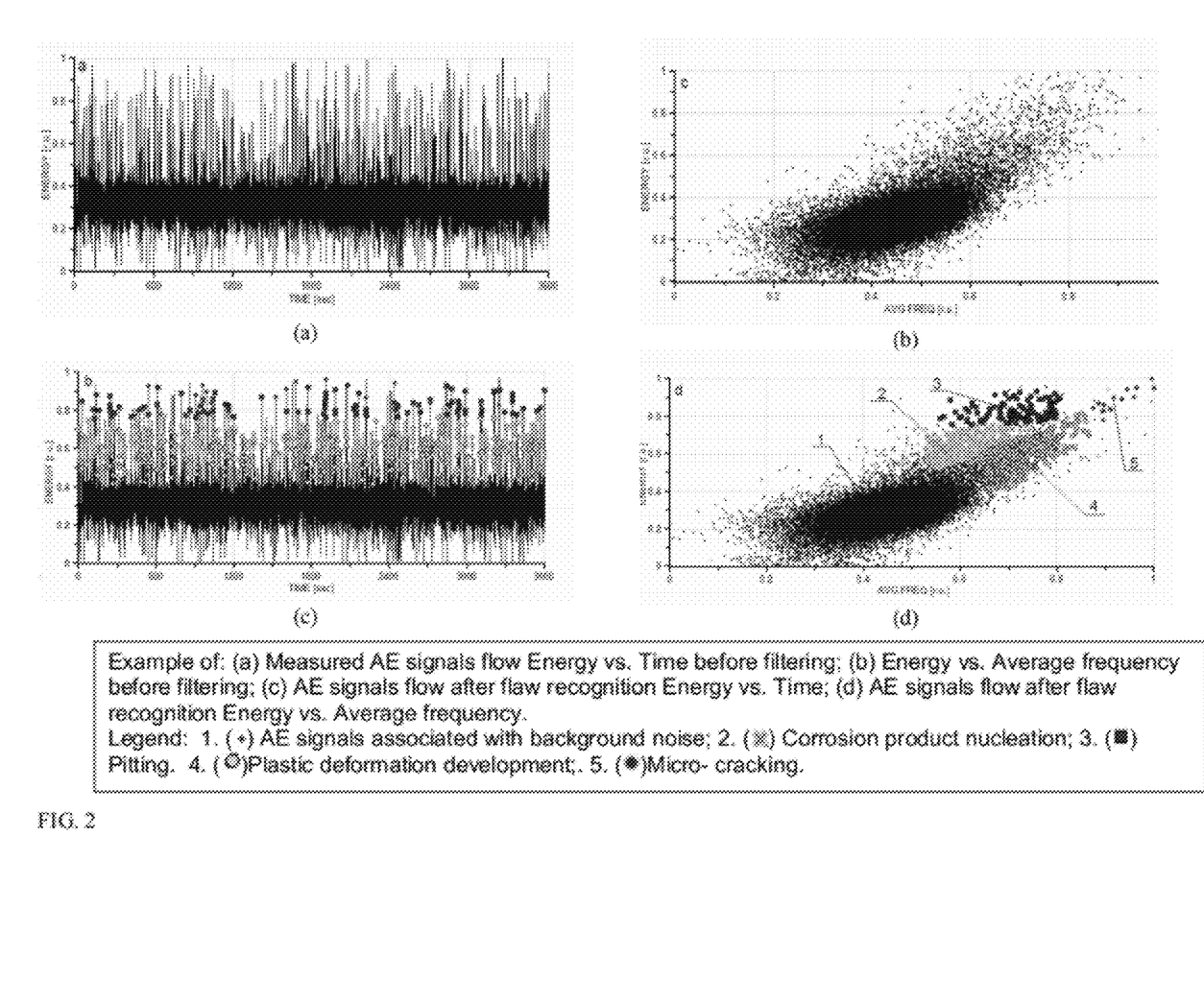
FIG. 2 illustrates an example of measured acoustic emission signals.
Figure 3:
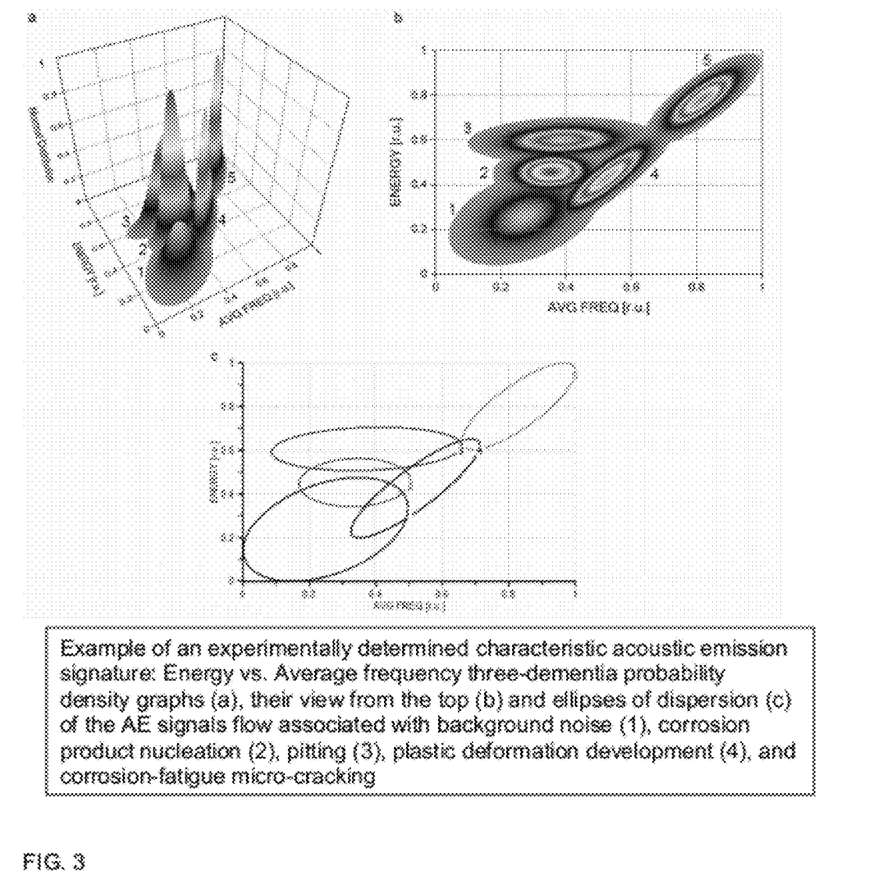
FIG. 3 illustrates an example of an experimentally determined characteristic acoustic emission signature.
Figure 4:
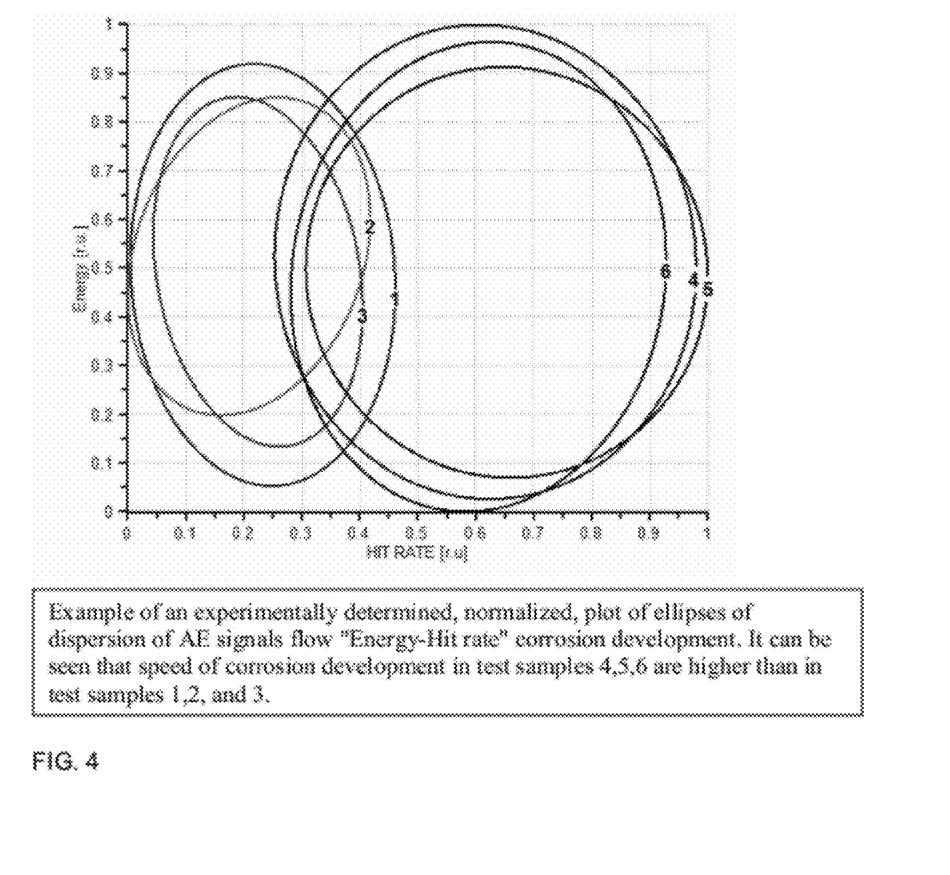
FIG. 4 illustrates an example of a normalized plot of AE signal energy vs. hit rate.

In an embodiment, each characteristic AE signature may be described using a statistical tool referred to as an "ellipse of dispersion", which term will be better understood by referring to FIGS. 2-4. FIG. 2a illustrates an exemplary plot of measured AE signals energy as a function of time, whereas FIG. 2b illustrates the same data where measured AE energy is plotted as a function of average frequency. The inventors have discovered that AE signals associated with different flaw development processes may have a distinguishable and repeatable relationship between, for example, energy and frequency. For example, in FIGS. 2c and 2d, the data presented in FIGS. 2a and 2b, respectively is annotated to distinguish background noise (1), from AE associated with four types of corrosion fatigue processes, specifically: corrosion product nucleation, (2), pitting (3), plastic deformation (4) and micro-cracking (5). It may be observed that AE signals associated with each process tend to be grouped in clusters, when viewed on a plot of, for example, energy vs. frequency. The respective clusters may be roughly delineated by elliptical shapes, as illustrated in FIG. 3, which also illustrates statistical information about the data points on a third dimension. The statistical information may include, for example, a metric related to probability that a signal having a particular measured frequency/energy relationship is correctly identified as being emitted from a particular source type. Thus, a characteristic AE signature may be described by an experimentally determined ellipse of dispersion that bounds a sheaf of AE signal properties.

Advantageously, a characteristic AE signature for a particular test article, and for each particular flaw development process may first be obtained in laboratory conditions. For example, test specimens may be exposed to specific environmental conditions to simulate operational stresses and corrosion fatigue development while measuring AE. Advantageously, a series of stress exposures and AE measurements may be made iteratively to characterize AE parameters as a function of flaw development. For example, a fatigue crack or appropriately shaped micro crack may be created in a specimen made from a steel used in the equipment to be the subject of QAE NDI. The specimen may then be tensioned to simulate operational equipment stresses, and/or exposed to high temperature. Stress levels, temperature, and surrounding moisture, for example, may be selected with a view toward accelerating corrosion fatigue fracture processes. AE may be measured during the foregoing exposure, followed by a metallurgical inspection. The above sequence may be repeated several times, thereby permitting establishment of a correlation of measured AE characteristics with kinetic characteristics of flaw development and fracture hazards.

In an embodiment, an intensity of a flaw development process may be determined by correlating an ellipse of dispersion of AE signal energy vs. hit rate constructed from measured data of the equipment under test with a (previously determined) characteristic ellipse. For example, referring now to FIG. 4, a normalized plot of AE signal energy vs. hit rate for test samples 4, 5, and 6 demonstrates that a speed of flaw development processes for those samples is higher than for samples 1, 2, and 3.

Figure 5:
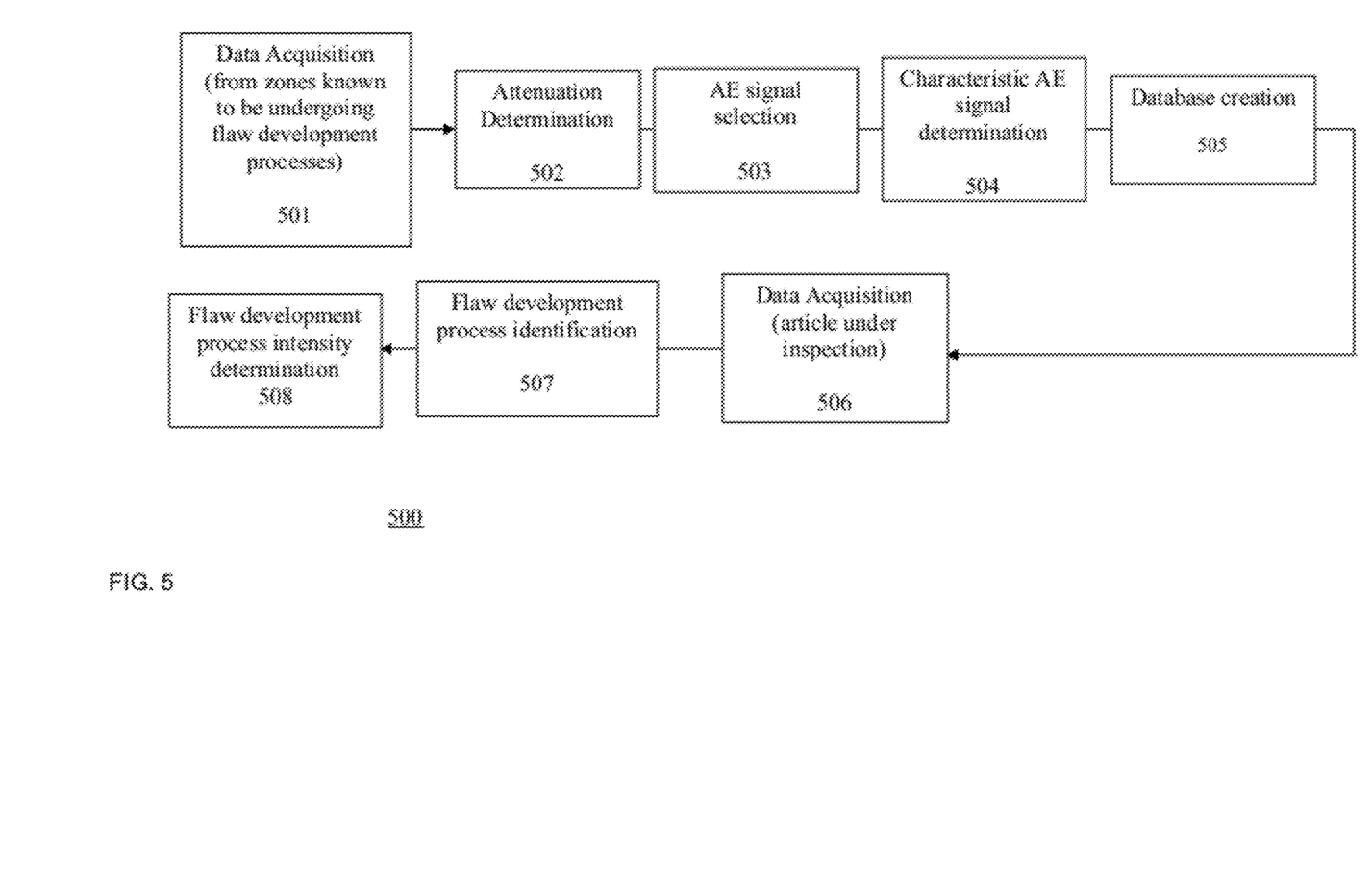
FIG. 5 presents a flow chart illustration of a method embodiment.

Referring now to FIG. 5, a method 500 for revealing, recognizing and assessing fracture hazards of flaw development processes will be described. In an embodiment, as described hereinbelow, a flaw development process such as corrosion product nucleation and development, pitting, plastic deformation development, and micro-cracking may be detected in equipment under inspection.

Data acquisition step 501 may consist of recording continuous and burst AE data in no less than six selected zones. The zones may be selected based on earlier reliable detection of one or more identified flaw development processes, such as corrosion product nucleation and development, pitting, plastic deformation development, and micro-cracking in the selected zones. The earlier reliable detection may have been based on visual, local NDI methods, or by metallurgical investigations. The acquired AE data may consist of AE signal characteristics of amplitude, energy, and frequency measured at each zone.

Figure 6:
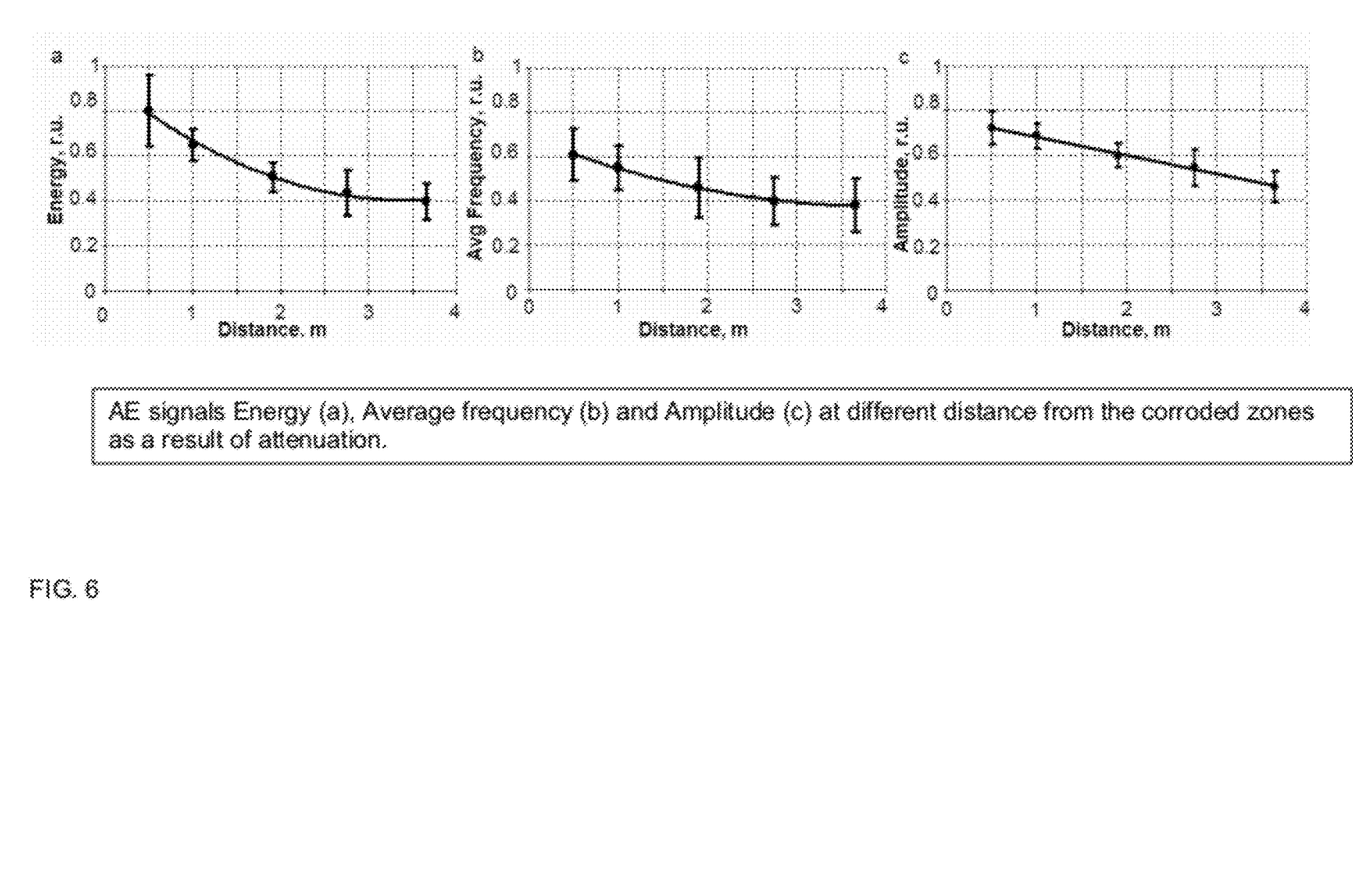
FIG. 6 illustrates an example of a plot of AE signal energy, average frequency and amplitude as a function of distance from a signal source.

Attenuation determination step 502 may consist of measuring attenuation of kinetics characteristics of flaw development at different distances from the selected zones. For example, AE signal energy, average frequency and/or amplitude may be plotted as a function of distance, as illustrated in FIG. 6 to determine AE signal transmission attenuation.

AE signal selection step 503 may consist of separating AE signals associated with flaw development processes from AE signals associated with background noise using a Gaussian shaped distribution. For example, as illustrated in FIG. 2, AE signals associated with corrosion product nucleation and development, pitting, plastic deformation development, and micro-cracking may be separated from background noise, using a Gaussian shaped distribution.

Characteristic AE signal determination step 504 may consist of determining, for at least one identified flaw development process, a characteristic AE signature. The characteristic AE signature may be determined by constructing a probability density graph and a number of ellipses of dispersion, as described hereinabove, with reference to FIG. 3. Advantageously, probability density graphs and ellipses of dispersion may be constructed for each flaw development process identified in step 501. In an embodiment, each ellipse of dispersion may bound a sheaf of AE signal properties associated with the characteristic AE signature. The sheaf of AE signal properties may be, for example, energy vs. average frequency, amplitude vs. average frequency, or energy vs. hit rate.

Database creation step 505 may consist of combining the results of steps 503 and 504 for a number of specific operational conditions.

Data acquisition step 506 may consist of measuring AE signals from each of a plurality of locations within the equipment under inspection. In an embodiment, AE sensors may be installed at the surface of the equipment such that zones of reliable data acquisition are overlapped, taking into account AE signal attenuation data acquired in step 502. Advantageously, sensors may be installed so as to include zones where flaw development processes are most suspected. Data acquisition of continuous and burst AE signals from the equipment may then be conducted.

Flaw development process identification step 507 may consist of comparing, for each location, measured AE signals, corrected taking into account attenuation, with the characteristic AE signatures in the database. Presence of a flaw development process may be identified, when the measured AE conforms to a characteristic AE signature in the database within a predetermined tolerance.

Flaw development process intensity determination step 508 may consist of comparing, for each type of developing flaw, a measured AE energy vs. hit rate with ellipses of dispersion, stored in the database, of energy vs. hit rate.

Thus, methods and systems for use of quantitative acoustic emission non-destructive inspection techniques for detecting the onset of flaw development processes and preventing fracture hazards have been described.

What is claimed is:

1. A method for revealing, recognizing and assessing fracture hazards of electro-chemical corrosion, pitting, and corrosion-fatigue, said method comprising:
  (i) detecting a presence of a flaw development process in an inspected equipment, said flaw development process comprising at least one of corrosion product nucleation and development, pitting, plastic deformation development, and micro-cracking, wherein said detecting comprises:
    (a) recording acoustic emission (AE) data of continuous AE and burst AE measured in a number of zones, said zones being known, as a result of at least one of visual inspection, local non-destructive inspection and metallurgical investigation, to be experiencing the flaw development process, said number of zones being at least six, said acquired AE data comprising AE signal characteristics of amplitude, energy, and frequency measured at each zone;

(b) determining AE signal transmission attenuation by recording AE data comprising AE signal characteristics of amplitude, energy, and frequency at different distances from each said zone, said AE signal transmission attenuation characterizing kinetics of flaw development as a function of distance from the zone;

(c) separating a plurality of AE signals associated with each flaw development process from background noise, using Gaussian shaped distribution;

(d) determining, for at least one selected flaw development process, a characteristic AE signature by constructing a probability density graph and a plurality of ellipses of dispersion, wherein:

each said ellipse of dispersion bounds a sheaf of AE signal properties associated with the characteristic AE signature; and the sheaf of AE signal properties is selected from the group comprising energy vs. average frequency, amplitude vs. average frequency, and energy vs. hit rate;

(e) creating a database of characteristic AE signatures by combining the information from each process described in (c), for a plurality of specific operational conditions;

(f) measuring AE signals from each of a plurality of locations within the equipment; and (ii) comparing, for each location, said measured AE signals, corrected for said attenuation, with the characteristic AE signatures in the database;

(iii) identifying a presence of the flaw development process only when the measured AE conforms to a characteristic AE signature in the database within a predetermined tolerance; and (iv) determining an intensity of the flaw development process by comparing a measured AE energy vs. hit rate with ellipses of dispersion of energy vs. hit rate from the database.

2. The method of claim 1, wherein the inspected equipment comprises at least one of
(i) a main steam (MS) piping, hot reheat (HRH) piping or cold reheat (CRH) piping of a fossil power plant,
(ii) Technological piping of a chemical plant, and (iii) other operating and large-scale high energy piping complex or components.

3. The method of claim 1, wherein said detecting step is a passive operation performed while avoiding use of an external excitation load source.

4. The method of claim 1, wherein the characteristic AE signature is an experimentally determined ellipse of dispersion.

5. A method for inspecting for fracture hazards in an equipment under inspection, said method comprising:

(i) detecting a presence of at least one flaw development process in the equipment wherein the flaw development process comprises at least one of corrosion product nucleation and development, pitting, plastic deformation development, and micro-cracking, wherein said detecting comprises:

(a) determining at least one characteristic acoustic emission (AE) signature, said characteristic AE signature being associated with a respective flaw development process;

(b) measuring AE signals from each of a plurality of locations within the equipment, said AE signals comprising continuous AE signals associated with at least one flaw development process, burst AE signals associated with at least one flaw development process, and background noise; and, for each location:

(1) separating at least one of the burst AE and the continuous AE from background noise;

(2) comparing said at least one of the burst AE and the continuous AE with the characteristic AE signature; and (3) identifying the presence of one or more respective flaw development processes associated with one or more of the plurality of locations only when the at least one of the burst AE and the continuous AE conforms to the characteristic AE signature within a predetermined tolerance; and (ii) determining that a fracture hazard exists, only when at least one of (a) a quantity of the identified flaw development processes exceeds a first predetermined threshold and (b) a magnitude of at least one of the identified flaw development processes exceeds a second predetermined threshold.

6. The method of claim 5, wherein the inspected equipment comprises at least one of (i) a main steam (MS) piping, hot reheat (HRH) piping or cold reheat (CRH) piping of a fossil power plant, (ii) technological piping of a chemical plant, and (iii) other operating and large-scale high energy piping complex or components.

7. The method of claim 5, wherein said detecting step is a passive operation performed while avoiding use of an external excitation load source.

8. The method of claim 5, wherein the at least one characteristic AE signature is an experimentally determined ellipse of dispersion.

9. The method of claim 8, wherein the experimentally determined ellipse of dispersion for each flaw development process is determined by analysis of data acquired of at least one of continuous and burst AE in a number of zones known to be experiencing the failure process.

10. The method of claim 9, wherein the experimentally determined ellipse of dispersion bounds a sheaf of AE signal properties associated with the characteristic AE signature.

11. The method of claim 10, wherein the sheaf of AE bounded signal properties comprises at least one of (i) energy vs. average frequency and (ii) amplitude vs. average frequency.

12. The method of claim 11, wherein the experimentally determined ellipse of dispersion is determined by measurements in a number of zones known to be undergoing flaw development processes, said number of zones being at least six.

13. The method of claim 5, wherein the at least one characteristic AE signature comprises an ellipse of dispersion relating AE signal energy vs. hit rate, and further comprising determining an intensity of the flaw development process by comparing a measured AE signal energy vs hit rate with said ellipse describing AE signal energy vs. hit rate.

14. A method for inspecting for fracture hazards in an equipment under inspection, said method comprising:

(i) detecting a presence of at least one flaw development process in the equipment wherein the flaw development process comprises at least one of corrosion product nucleation and development, pitting, plastic deformation development, and micro-cracking, wherein said detecting comprises:

(a) determining at least one characteristic acoustic emission (AE) signatures associated with flaw development, said characteristic AE signatures being associated with a respective flaw development process;

(b) comparing at least one measured AE signals associated with flaw development with the characteristic AE signatures, said measured AE signal having been obtained from a respective location within the equipment, and comprising continuous AE, burst AE, and background noise; and, for each respective location:

(1) separating at least one of the burst AE and the continuous AE signals associated with flaw development from background noise;

(2) comparing said at least one of the burst AE and the continuous AE signals associated with flaw development with the characteristic AE signature; and    (3) identifying the presence of the respective flaw development process, only when the measured AE signals conforms to the characteristic AE signatures within a predetermined tolerance; and (ii) determining that a fracture hazard exists, only when at least one of (a) a quantity of the identified flaw development processes exceeds a first predetermined threshold and (b) a magnitude of at least one of the identified flaw development processes exceeds a second predetermined threshold.

15. The method of claim 14, the inspected equipment comprises at least one of (i) a main steam (MS) piping, hot reheat (HRH) piping or cold reheat (CRH) piping of a fossil power plant, (ii) technological piping of a chemical plant, and (iii) other operating and large-scale high energy piping complex or components.

16. The method of claim 14, wherein said measured AE is obtained by a passive operation, said passive operation being performed while avoiding use of an external excitation load source.

17. The method of claim 14, wherein the at least one characteristic AE signature is an experimentally determined ellipse of dispersion.

18. The method of claim 17, wherein the experimentally determined ellipse of dispersion for each flaw development process is determined by analysis of data acquired of at least one of continuous and burst AE in a number of zones known to be experiencing the failure process.

19. The method of claim 18, wherein the experimentally determined ellipse of dispersion bounds a sheaf of AE signal properties associated with the characteristic AE signature.

20. The method of claim 19, wherein the sheaf of AE bounded signal properties comprises at least one of (i) energy vs. average frequency and (ii) amplitude vs. average frequency.

21. The method of claim 20, wherein the experimentally determined ellipse of dispersion is determined by measurements in a number of zones known to be undergoing flaw development processes, said number of zones being at least six.

22. The method of claim 14, further comprising determining an intensity of the flaw development process by comparing at least one ellipse of dispersion characterizing AE energy vs hit rate constructed from signals measured in different zones of piping with ellipses of dispersion of energy vs. hit rate from the database.

* * * * *